(12) United States Patent
Werninger et al.

(10) Patent No.: US 6,864,388 B2
(45) Date of Patent: Mar. 8, 2005

(54) PROCESS FOR PREPARING SALTS OF METHALLYLSULFONIC ACID

(75) Inventors: Claus York Werninger, Itzehoe (DE);
Lothar Kerker, Duelmen (DE);
Hartmut Steinbeisser, Marl (DE);
Wilfried Bueschken, Haltern (DE);
Franz-Felix Kuppinger, Marl (DE);
Peter Ernst Esser, Aschheim (DE)

(73) Assignee: OXENO Olefinchemie GmbH, Marl (DE)

( * ) Notice: Subject to any disclaimer, the term of this patent is extended or adjusted under 35 U.S.C. 154(b) by 423 days.

(21) Appl. No.: 10/200,763

(22) Filed: Jul. 24, 2002

(65) Prior Publication Data

US 2003/0070928 A1 Apr. 17, 2003

(30) Foreign Application Priority Data

Jul. 24, 2001 (DE) .......................................... 101 35 907

(51) Int. Cl.$^7$ ............................. C07C 3/00; B01D 61/44
(52) U.S. Cl. ........................ 562/123; 562/124; 204/523
(58) Field of Search ......................... 204/523; 562/123, 562/124

(56) References Cited

FOREIGN PATENT DOCUMENTS

| DE | 1 804 833 | | 10/1968 |
| DE | 2334768 | * | 2/1974 |
| GB | 1 321 821 | * | 4/1973 |

* cited by examiner

*Primary Examiner*—Arun S. Phasge
(74) *Attorney, Agent, or Firm*—Oblon, Spivak, McClelland, Maier & Neustadt, P.C.

(57) ABSTRACT

A process for preparing salts of methallylsulfonic acid in which the reaction mixture produced from the sulfonation is diluted with water and neutralized with a base.

18 Claims, No Drawings

PROCESS FOR PREPARING SALTS OF METHALLYLSULFONIC ACID

BACKGROUND OF THE INVENTION

1. Field of the Invention

The present invention relates to a process for preparing salts of methallylsulfonic acid by sulfonation of isobutene by means of Lewis base-sulfur trioxide complexes and subsequent neutralization.

2. Description of the Background

Salts of methallylsulfonic acid are used as comonomers in the synthesis of fiber intermediates, in particular for the modification of polyacrylonitriles. Furthermore, these salts are employed in the production of dispersions.

Salts of methallylsulfonic acid are prepared industrially by two different routes starting from isobutene:

In the first synthetic route, isobutene is reacted with chlorine to form the intermediate methallyl chloride. This compound reacts with sulfites to give the target products. For example, the reaction of methallyl chloride with sodium sulfite gives sodium methallylsulfonate and sodium chloride. Disadvantages of this synthesis are that the molar yield of target product is only 85% based on isobutene and inorganic chlorides are formed as coproducts and organic chlorine compounds are formed as by-products.

In the other synthetic route, sulfur trioxide is added onto isobutene and the resulting methallylsulfonic acid is subsequently reacted with a base to give the corresponding salt. Many different processes for this reaction sequence are known from the literature. Owing to the improved selectivity of the formation of methallylsulfonic acid, the sulfonation of isobutene is carried out using not sulfur trioxide but a complex of sulfur trioxide and a Lewis base.

Industrial processes for preparing salts of methallylsulfonic acid, in general the sodium salt, comprise the following steps:

(a) Preparation of a solution of a complex consisting of sulfur trioxide and a Lewis base and, if desired, a solvent
(b) Sulfonation of isobutene using the solution prepared in step (a)
(c) Conversion of the acids formed in step (b) into their salts
(d) Isolation and purification of the methallylsulfonate
(e) Recovery and purification of the complexing agent and, if desired, a solvent.

The processes employed in industry can be divided into two groups. In the first group, the preparation of the $SO_3$-Lewis acid complex and its reaction with isobutene is carried out in an additional solvent. Customary solvents are ethylene glycol dimethyl ether and halogenated hydrocarbons such as methylene chloride, chloroform and 1,2-dichloroethane. A disadvantage of these processes is not only the Lewis acid but also a solvent have to be separated off and purified before recirculation to the process. Furthermore, losses of solvent result from chemical reactions. For example, halogenated hydrocarbons are hydrolyzed to a slight extent during the neutralization. This forms organic by-products which have to be separated off and an aqueous wastewater stream containing chlorides. These materials incur additional disposal costs.

In the second group of processes, no additional solvent is used. The liquid Lewis acid is used in excess and serves not only as complexing agent but also as solvent or suspension medium for the sulfur trioxide-Lewis acid complex.

DE 1 804 833 discloses a process for preparing salts of methallylsulfonic acid without use of an additional solvent. Here, isobutene is reacted with a complex of sulfur trioxide and an N,N-dialkyl-substituted amide of an aliphatic carboxylic acid or an N-alkylated lactam in an excess of the complexing agent as reaction medium at temperatures of from −20 to +60° C., using at least one mol of isobutene per mol of sulfur trioxide. The reaction mixture obtained is neutralized by means of an aqueous base. The neutralization step should be carried out in such a way that no secondary reactions occur. The only information given in respect of such a reaction procedure is the use of dilute caustic alkalis or weak alkalis such as sodium carbonate for neutralizing the reaction mixture. The aqueous phase is completely or partly evaporated and the target product is separated off. The yield of yellowish crude product, based on sulfur trioxide, is up to 97%. The yield of pure, white product is at least 80%. The formation of by-products can occur in the sulfonation reaction or the neutralization; particular mention may be made of the hydrolysis of the complexing agent as secondary reaction which contaminates the product and at the same time makes the economics of the process questionable as a result of the loss of material.

SUMMARY OF THE INVENTION

It is an object of the present invention to develop an economical process for preparing salts of methallylsulfonic acid in which the formation of by-products is reduced and the yield of target product is increased.

It has now surprisingly been found that the loss of complexing agent, the consumption of alkali and the outlay for separating off the target product can be reduced when the reaction mixture formed in the sulfonation of isobutene by means of a sulfur trioxide-Lewis base complex is diluted with water prior to neutralization of the mixture.

The present invention accordingly provides a process for preparing salts of methallylsulfonic acid by reacting isobutene with a sulfur trioxide-Lewis base complex, neutralizing the resulting reaction mixture by means of a base and separating off the salt of methallylsulfonic acid, which comprises (a) sulfonating isobutene with a sulfur trioxide-Lewis base complex at a temperature of from −20 to 80° C. and a pressure of from 1 to 15 bar,
(b) diluting the reaction mixture from (a) with water,
(c) neutralizing the diluted reaction mixture from (b) to a pH of 6–8 with a base, and
(d) isolating the salt of methallylsulfonic acid from the neutralized reaction mixture from A more complete appreciation of the invention and many of the attendant advantages thereof will be readily obtained as the same becomes better understood by reference to the following detailed description.

DETAILED DESCRIPTION OF THE INVENTION

The sulfonation can be carried out in an organic solvent, e.g. a Lewis base. The Lewis bases used as complexing agent and solvent can be different or identical.

In the process of the invention, preference is given to using N,N-dialkylated carboxamides such as N,N-diethylacetamide, N,N-dimethylacetamide and N,N-dimethylformamide (DMF), N-alkylated lactams such as N-methylpyrrolidone, dialkyl sulfoxides or cyclic sulfoxides, for example dimethyl sulfoxide, cyclic sulfones or dialkyl sulfones and cyclic ethers such as dioxane as complexing agent for sulfur trioxide and, if desired, as solvent. A preferred Lewis base as complexing agent and solvent is N,N-dimethylformamide (DMF).

It is also possible to use a mixture of two or more of the above mentioned Lewis bases for the complexation of sulfur trioxide or as solvent. However, it is advantageous to use only one Lewis base because this makes it easier to recover the auxiliaries.

The sulfur trioxide complex can be prepared using liquid sulfur trioxide, gaseous sulfur trioxide which has, for example, been distilled from oleum or other gas mixtures in which sulfur trioxide is present.

The preparation of the complex can be carried out using gas mixtures which comprise sulfur trioxide together with other gases which do not react with the complexing agent under the reaction conditions of the complexation or, if they do, form only complexes which are significantly weaker than the corresponding sulfur trioxide complexes.

Such gas components can be, for example, nitrogen, oxygen, carbon dioxide or sulfur dioxide. A preferred feed gas is the output gas from the catalytic reactor of a sulfuric acid plant, which has, for example, the following composition: 7.5% by volume of $SO_3$, 0.2% by volume of $SO_2$, 13.0% by volume of $O_2$ and 79.3% by volume of $N_2$. However, it should be emphasized that the gas from the catalytic reactor can also have a completely different composition. In the preparation of $SO_3$ complexes in the process of the present invention, particular preference is given to using catalytic reactor gases having a relatively high $SO_3$ content and a low $SO_2$ content. This has the advantage that, owing to the smaller amount of off-gas, less complexing agent is carried out and the formation of the $SO_2$ complex is low. The formation of the $SO_2$ complex is undesirable since it results in an increased consumption of alkali in the neutralization and the resulting sulfites have to be separated off from the target product.

To obtain a homogeneous solution of the sulfur trioxide-Lewis base complex in the Lewis base, the Lewis base has to be used in excess. When using DMF as complexing agent and solvent, the molar ratio of DMF to $SO_3$ is in the range from 100/1 to 5/1, in particular in the range from 20/1/to 6/1.

Sulfur trioxide reacts with water to form sulfuric acid which does not react with isobutene to form methallylsulfonic acid under sulfonation conditions, but can cause secondary reactions. In the neutralization, it forms sulfates which have to be separated off like the other by-products. To obtain a high yield, it is therefore necessary for the Lewis base used to be as free of water as possible, e.g. as a result of drying over molecular sieves. This also applies to the Lewis base which is separated off from the process and is returned after work-up. Furthermore, care should be taken to ensure that the Lewis base does not contain other protic compounds, for example alcohols, or other substances which could react with sulfur trioxide as impurities, because this reduces the yield and complicates the work-up.

Complex formation can be carried out batchwise or continuously in a stirred vessel, a cascade of stirred vessels or in one or more bubble column reactors. When liquid sulfur trioxide is used, the complexation is carried out in a stirred vessel or a plurality of stirred vessels connected in series. The residence times are generally from 1 to 3 hours.

If a sulfur trioxide gas mixture having a high proportion of inert gas, for example a gas from the catalytic reactor of a sulfuric acid plant, is used, the complexation is preferably carried out in a bubble column or a plurality of bubble columns connected in series. The reaction can proceed under superatmospheric pressure or atmospheric pressure. To achieve substantially complete absorption of the sulfur trioxide and minimize the losses of Lewis base, the rate at which the gas is introduced is kept small. The reaction time is from 1 to 10 hours, preferably from 2 to 8 hours. The reaction temperatures are in the range from 5 to 50° C., in particular in the range from 8 to 27° C., very particularly preferably in the range from 10 to 15° C.

The sulfonation can be carried out using an isobutene excess based on the $SO_3$ used of from 5 to 60 mol %, in particular from 5 to 20%. Isobutene is firstly added in liquid or gaseous form to the sulfur trioxide-Lewis base complex, optionally in one of the above mentioned solvents, at temperatures of from −20 to 25° C., in particular from 5.0 to 10° C. The mixture is subsequently heated and the reaction is completed in the temperature range up to 80° C., preferably from 45 to 55° C. To keep the isobutene in solution, the reaction is carried out under the autogenous pressure of isobutene.

The mixing of the reaction components or process of the invention itself can be carried out batchwise or continuously.

In a batch process in a stirred vessel, isobutene is, for example, introduced in gaseous or preferably liquid form into a sulfur trioxide-DMF solution at a temperature in the range from −20 to 25° C., in particular from 5 to 10° C. and very particularly preferably from 7 to 9° C., over a period of from 0.2 to 1.0 h, in particular from 0.4 to 0.6 h. The contents of the reactor are brought to 43–48° C., in particular 45–46° C., over a period of 0.05 to 1.0 h, in particular from 0.15 to 0.30 h. After a further reaction time of 0.05 to 0.3 h at this temperature, a final temperature of 49–52° C. is set and this is kept constant for from 0.9 to 1.5 h, in particular from 1.0 to 1.3 h.

A continuous process could, for example, be carried out in the following manner:

isobutene is mixed into a sulfur trioxide-DMF solution under pressure in the temperature range from 5 to 10° C. by means of a static mixer. The reaction mixture is brought to 30° C. in a coiled tube and subsequently reacted in two tube stirred reactors connected in series, of which the first is operated at 45° C. and the second is operated at 50° C. Another possibility would be to react the reaction mixture in a three-stage cascade of stirred vessels with a residence time of half an hour in each, with the first reactor being operated at a temperature of 45° C. and the other two being operated at 50° C.

In both variants, the reaction mixture is depressurized to atmospheric pressure after the sulfonation is complete. If desired, a slight vacuum is applied. Part of the isobutene used in excess can be recovered from the depressurization gas and returned to the process.

If desired, the depressurization and the recovery of the excess isobutene can be carried out after addition of water or after neutralization.

A further possible way of separating off the unreacted isobutene is for the sulfonation mixture either to be diluted with water or to be diluted with water and subsequently neutralized and the isobutene then to be taken off as second liquid phase under the autogenous pressure of isobutene.

In the process of the invention, the above reaction mixture in which the methallylsulfonic acid is present is diluted with water prior to neutralization by means of an alkali. This can be carried out either batchwise or continuously. Here, water can be added to the reaction mixture from the sulfonation while mixing, but it is also possible to use the reverse procedure, i.e. to add the reaction mixture from the sulfonation to the water. Furthermore, it is also possible to mix the reaction mixture from the sulfonation directly with water in the specified ratio.

Water is, for example, introduced over a period of from 0.1 to 1.0 h, in particular from 0.2 to 0.5 h. These time period ranges include all specific values and subranges therebetween, such as 0.3, 0.4, 0.6, 0.7, 0.8, and 0.9 h. The temperature of the mixture is maintained at from 20 to 80° C., in particular from 30 to 55° C. These temperature ranges include all specific values and subranges therebetween, such as 25, 35, 40, 45, 50, 60, 65, 70 and 75° C. An additional mixing time is not necessary. The amount of water added depends on the amount of sulfur trioxide used for the sulfonation. Dilution is carried out using from 2 to 10 kg of water, in particular from 3 to 5 kg of water, per 1 kg of sulfur trioxide, which corresponds to a mass ratio of from 1:2 to 1:10 or from 1:3 to 1:5. These ranges for the amount of water include all specific values and subranges therebetween, such as 4, 6, 7, 8, and 9 kg of water per 1 kg of sulfur trioxide. Accordingly, these ranges for the mass ratio include all specific values and subranges therebetween, such as 1:4, 1:6, 1:7, 1:8, and 1:9.

The neutralization of the acidic substances such as sulfonic acids and sulfuric acid is effected by addition of inorganic or organic bases such as basic compounds of the alkali metals and alkaline earth metals. These are used in the form of their carbonates, hydrogencarbonates or hydroxides. The neutralizing agent can be used in solid form or preferably as a solution, in particular an aqueous solution. The aqueous solutions can have concentrations of from 5 to 40%. Particular preference is given to using aqueous sodium hydroxide solution having a concentration in the range from 1 to 30%, very particularly preferably from 20 to 30%. The neutralizing agent is added in such an amount that the resulting mixture has a pH of from 6 to 8, in particular from 6.5 to 7.5. In the most favorable case, one mol of a monovalent base is necessary per mol of sulfur trioxide. However, since part of the sulfur trioxide could have reacted to form sulfuric acid and other acidic substances apart from sulfonic acid, for example sulfur dioxide, may be present, the amount of alkali required is usually greater.

The cation of the base represents the cation of the resulting salt of methallylsulfonic acid.

If salts of methallylsulfonic acid with other cations are desired, these can be prepared by ion exchange. For example, cation exchange using a cation exchanger can be carried out.

The neutralization is carried out under pH control at a temperature in the range from 20 to 80° C., in particular from 40 to 60° C. The neutralization time is from 0.1 to 1.0 h, in particular from 0.2 to 0.7 h.

The liquid, neutral reaction mixture is generally homogeneous and consists essentially of water, Lewis base, methallylsulfonate, other sulfonates and possibly sulfites and decomposition products of the Lewis base.

The target product, viz. the desired salt of methallylsulfonic acid, can be isolated from this solution in various ways:

a) The neutralized reaction mixture is concentrated by distillation, i.e. evaporated, and the pure target product is obtained from the residue, if desired after washing with water, by recrystallization from a solvent or solvent mixture in which the Lewis base used for the reaction does not have to be present.
b) The neutralized reaction mixture is concentrated by distillation so that the target product crystallizes out as a result of the evaporation. The product which has been separated off is washed and/or recrystallized if desired.
c) The neutralized reaction mixture is cooled and the resulting crystals are separated off.
d) The neutralized reaction mixture is separated from the Lewis base by extraction. The target product is isolated from the remaining aqueous phase by partial evaporation and crystallization.
e) The target product is separated off from the neutralized reaction mixture as an aqueous solution by means of electrodialysis. The target product is isolated from the aqueous solution by concentration by distillation and crystallization.

When sodium methallylsulfonate is the target product and DMF is used as Lewis base in the process of the invention, the product is preferably isolated by crystallizing it out by cooling after removal of the water and part of the DMF.

The concentration by distillation is preferably carried out in the temperature range from 110° C. to 140° C., in particular in the range from 110° C. to 120° C. From 50 to 70%, in particular from 50 to 60%, very particularly preferably from 50 to 56%, of the reaction mixture are distilled off. The distillate, viz. a water/DMF mixture, comprises predominantly water.

The reaction mixture, which may have been concentrated, is then cooled, for example in a crystallizer provided with a stirrer. Crystallization commences at about 110° C. To increase the crystallization yield, the solution is cooled to from 20 to 30° C. To obtain pure and readily filterable crystals, it is advantageous to cool the solution slowly. In the temperature range from 110° C. to 80° C., a cooling rate of from 5 to 20° C./h, in particular from 5 to 10° C./h, is advantageous. In the temperature range from 80° C. to the final temperature, the cooling rate is 20–50° C./h, in particular from 25 to 35° C./h.

Alternatively, the salt of methallylsulfonic acid, e.g. sodium methallylsulfonate, can be separated off from an aqueous DMF solution by electrodialysis in the temperature range from 20° C. to 100° C., in particular in the range from 20° C. to 60° C., using ion exchange membranes. This gives a solution (concentrate) consisting mainly of the desired salt (e.g. sodium methallylsulfonate) and water and a solution (retentate) consisting mainly of DMF and water. During the electrodialysis, the concentration of the target product increases. To prevent crystallization of the target product and coating or blocking of the membrane, it can be advantageous to increase the temperature within the above mentioned range.

If the aqueous methallylsulfonate solution is not to be used as such, the target product can be separated off from it by crystallization, if appropriate after further concentration by distillation. Crystallization is carried out using the above mentioned cooling rates.

The crystals are separated from the mother liquor by filtration or by centrifugation. The crystals can be washed with a solvent, in particular water. If water is used for washing, the amount of water employed for washing is from 5 to 30%, preferably from 10 to 20%, of the mass of the crystals. After drying, the crystals are composed of over 99%, preferably over 99.5%, of the desired methallylsulfonate.

The mother liquor and the washings can be concentrated either separately or together and returned to the crystallizer. However, it is also possible to concentrate these streams together with the neutralized sulfonation mixture.

Part of the mother liquor and/or the washings is discharged to remove by-products. This is advantageously done, particularly in the case of the mother liquor, after the concentration step.

The Lewis base obtained during concentration of the neutralized reaction mixture, i.e. the combined vapors of the retentate from the electrodialysis, which consist mainly of water and Lewis base, can be separated by distillation into water, Lewis base and by-products. By-products are, for example, dimethylamine formed by hydrolysis of Lewis base.

The recovered Lewis base can be returned to the process after removal of traces of water, for example by drying over molecular sieves. The water obtained in the fractional distillation can be utilized for dilution of the sulfonation mixture, for preparation of the aqueous alkali and/or as washing liquid.

The salt prepared, in particular sodium methallylsulfonate, can be dried and used as free-flowing crystalline material or be dissolved in water and used as an aqueous solution. Drying is carried out by known methods.

The salts of methallylsulfonic acid, in particular the sodium salt, prepared by the process of the invention are used as comonomers in the preparation of polymer dispersions and fiber intermediates, for example modified polyacrylonitrile. The incorporation of a methallylsulfonate into the polymer improves its ability to be dyed.

The process of the invention has the following advantages:

Only a small amount of complexing agent is lost, which keeps materials costs low. The small amounts of by-products make it easier for the target product to be separated off inexpensively and for the complexing agent to be recovered in pure form. Furthermore, it is possible to utilize an inexpensive gas from the catalytic reactor of a sulfuric acid plant as sulfur trioxide source for the preparation of the sulfur trioxide-Lewis base complex.

EXAMPLES

Having generally described this invention, a further understanding can be obtained by reference to certain specific examples which are provided herein for purposes of illustration only and are not intended to be limiting unless otherwise specified.

Example 1

Preparation of a Sulfur Trioxide-DMF Complex in DMF

Gas from the catalytic reactor of a sulfuric acid plant containing 5.24% by volume of sulfur trioxide was passed for 10 hours at a flow rate of 158 l/h into 3.3 kg of DMF which had been dried over molecular sieves. The reaction temperature was 10° C. 98.1% of the sulfur trioxide were absorbed, so that a solution containing 5.14 mol of sulfur trioxide/DMF complex was formed.

Example 2

Sulfonation 317 g (5.654 mol) of liquid isobutene were metered into the solution of the sulfur trioxide-DMF complex prepared in Example 1 at 8° C. over a period of 0.5 h while stirring. A pressure of 2.2–2.3 bar was established. The reaction mixture was heated to 45–46° C. over a period of 0.5 h. After 0.2 h at this temperature, the mixture was brought to 50° C. and stirred at 50° C. for 1.3 h.

Example 3 Comparative

Neutralization of the Reaction Solution

The reaction solution obtained from Example 2 was neutralized by adding 30% strength aqueous sodium hydroxide dropwise at 50° C. over a period of 0.5 h. The yield of sodium methallylsulfonate in the reaction mixture is 95.2% based on the sulfur trioxide-DMF complex. 330 g of DMF (10%) were lost as a result of hydrolysis.

Example 4 Inventive

The reaction mixture obtained from Example 2 was admixed at 50° C. with 1.6 kg of water. The mixture was subsequently neutralized at 50° C. by means of 30% strength aqueous sodium hydroxide. The yield of sodium methallylsulfonate in the reaction mixture was likewise 95.2% based on the sulfur trioxide-DMF complex. The loss of DMF as a result of hydrolysis was less than 0.3%.

Comparison of Example 4 with Example 3 shows that loss of DMF as a result of hydrolysis can be prevented virtually completely in the process of the invention by addition of water prior to the neutralization.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 101 35 907.1, filed on Jul. 24, 2001, and incorporated herein by reference.

What is claimed is:

1. A process for preparing salts of methallylsulfonic acid, which comprises:
    (a) sulfonating isobutene with a sulfur trioxide-Lewis base complex at a temperature of from −20 to 80° C. and a pressure of from 1 to 15 bar,
    (b) diluting the reaction mixture from (a) with water,
    (c) neutralizing the diluted reaction mixture from (b) to a pH of 6–8 with a base, and
    (d) isolating the salt of methallylsulfonic acid from the neutralized reaction mixture from (c).

2. The process of claim 1, wherein the Lewis base simultaneously serves as a solvent.

3. The process of claim 1, wherein the Lewis base is selected from the group consisting of N,N-dialkylated carboxamides, N-alkylated lactams, cyclic sulfoxides, cyclic sulfones, dialkyl sulfones, and cyclic ethers.

4. The process of claim 1, wherein (b) is conducted at a temperature of 20–80° C.

5. The process of claim 1, wherein (b) is conducted at a temperature of 30–55° C.

6. The process of claim 1, further comprising distilling the neutralized reaction mixture from (c).

7. The process of claim 6, further comprising purifying the Lewis base from the distilled reaction mixture by distillation, and recycling the distilled Lewis base to the process.

8. The process of claim 1, further comprising electrodialyzing the neutralized reaction mixture from (c).

9. The process of claim 8, further comprising purifying the Lewis base from the electrodialyzed reaction mixture by distillation, and recycling the distilled Lewis base to the process.

10. The process of claim 9, wherein the Lewis base is recycled to the process after drying.

11. The process of claim 1, wherein the salt of methallylsulfonic acid is crystallized from the reaction mixture at a temperature of 20–30° C.

12. The process of claim 1, wherein in (a) the isobutene is added to the sulfur trioxide-Lewis base complex at a temperature of from −20 to 25° C. and subsequently heated to 52° C.

13. The process of claim 1, wherein the base is selected from the group consisting of carbonates, hydrogencarbonates, and hydroxides of the alkali metals or alkaline earth metals, wherein the base is a solid or an aqueous solution.

14. The process of claim 1, wherein the sulfonation is carried out using a 5–60% molar excess of isobutene based on the sulfur trioxide-Lewis base complex.

15. The process of claim 1, wherein the water is introduced over period of from 0.1 to 1.0 h 16. The process of claim 1, wherein the water is introduced over a period of from 0.2 to 0.5 h.

17. The process of claim 1, wherein 2 to 10 kg of the water per 1 kg of the sulfur trioxide is added.

18. The process of claim 17, wherein 3 to 5 kg of the water per 1 kg of the sulfur trioxide is added.

* * * * *